Figure 1:
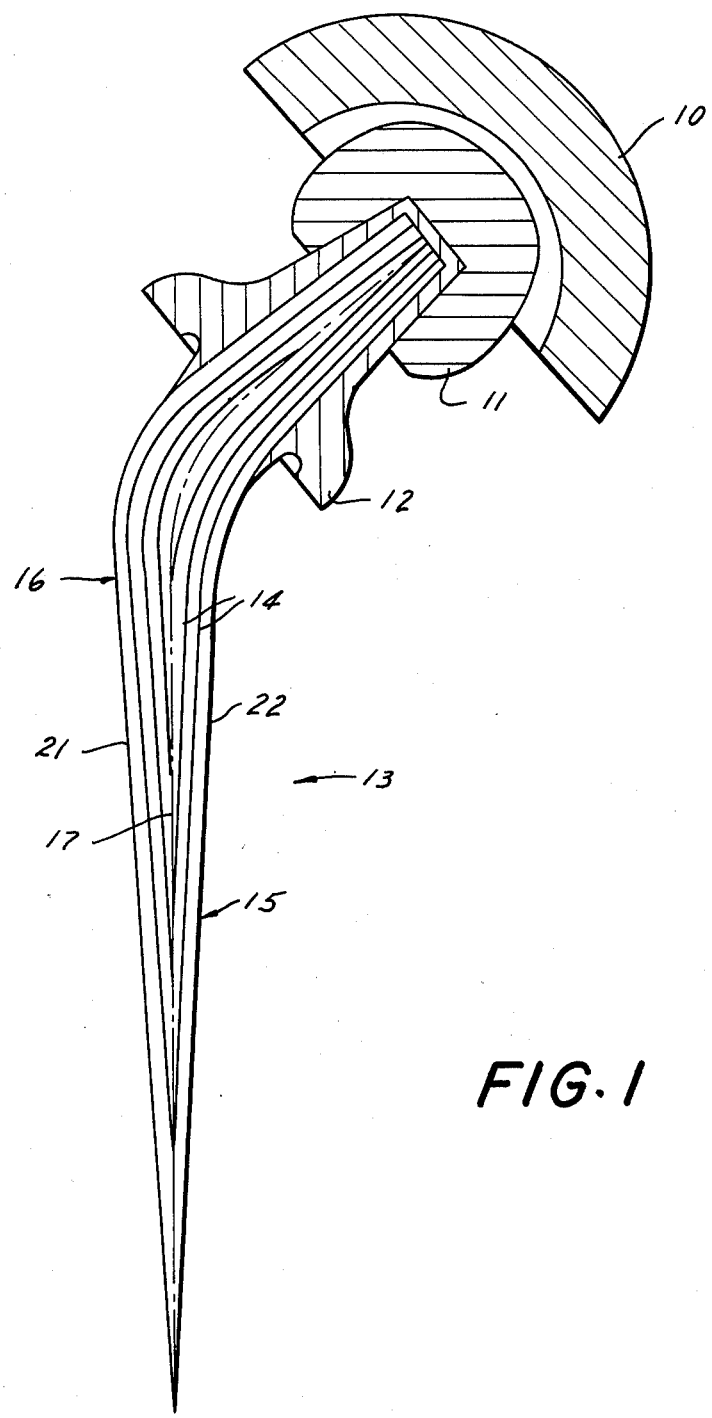

United States Patent [19]

Heissler et al.

[11] 4,221,623

[45] Sep. 9, 1980

[54] METHOD OF MANUFACTURING FIBER-REINFORCED PLASTIC BODIES

[75] Inventors: Herbert Heissler, Munich; Horst Wurtinger, Furstenfeldbruck; Karl H. Schaab, Kaufbeuren, all of Fed. Rep. of Germany

[73] Assignee: Maschinenfabrik Augsburg-Nurnberg Aktiengesellschaft, Munich, Fed. Rep. of Germany

[21] Appl. No.: 961,595

[22] Filed: Nov. 17, 1978

[30] Foreign Application Priority Data

Dec. 1, 1977 [DE] Fed. Rep. of Germany ....... 2753568

[51] Int. Cl.² .................. B65H 81/00; A61F 1/00
[52] U.S. Cl. .................. 156/169; 3/1.91; 3/1.913; 156/174; 156/180; 156/182; 156/264; 428/375; 428/397
[58] Field of Search ............... 156/166, 169, 175, 174, 156/180, 182, 264, 193, 172, 245, 212, 214, 228, 296; 264/258, 257, 152, 163, 137; 3/1.912, 1.913, 1.9; 428/375, 398, 397, 399; 52/729, 720, 721, 732, 730, 734

[56] References Cited

U.S. PATENT DOCUMENTS

| 3,107,189 | 10/1963 | Hill ........................................ 156/245 |
| 4,020,202 | 4/1977 | Kreft ..................................... 428/398 |

Primary Examiner—Michael W. Ball
Attorney, Agent, or Firm—Alan H. Levine

[57] ABSTRACT

A method of manufacturing a fiber-reinforced plastic body of irregular geometrical shape including winding a ring of fibers such that different sections of the ring around its periphery correspond in contour to sections of the body. The sections of the ring are cut from the remainder of the ring, and the sections joined together, such as by bonding to each other, to form the final body. The cut sections may be mechanically processed before joining them together. The fibers run approximately parallel to the outer contour of the finished body.

5 Claims, 2 Drawing Figures

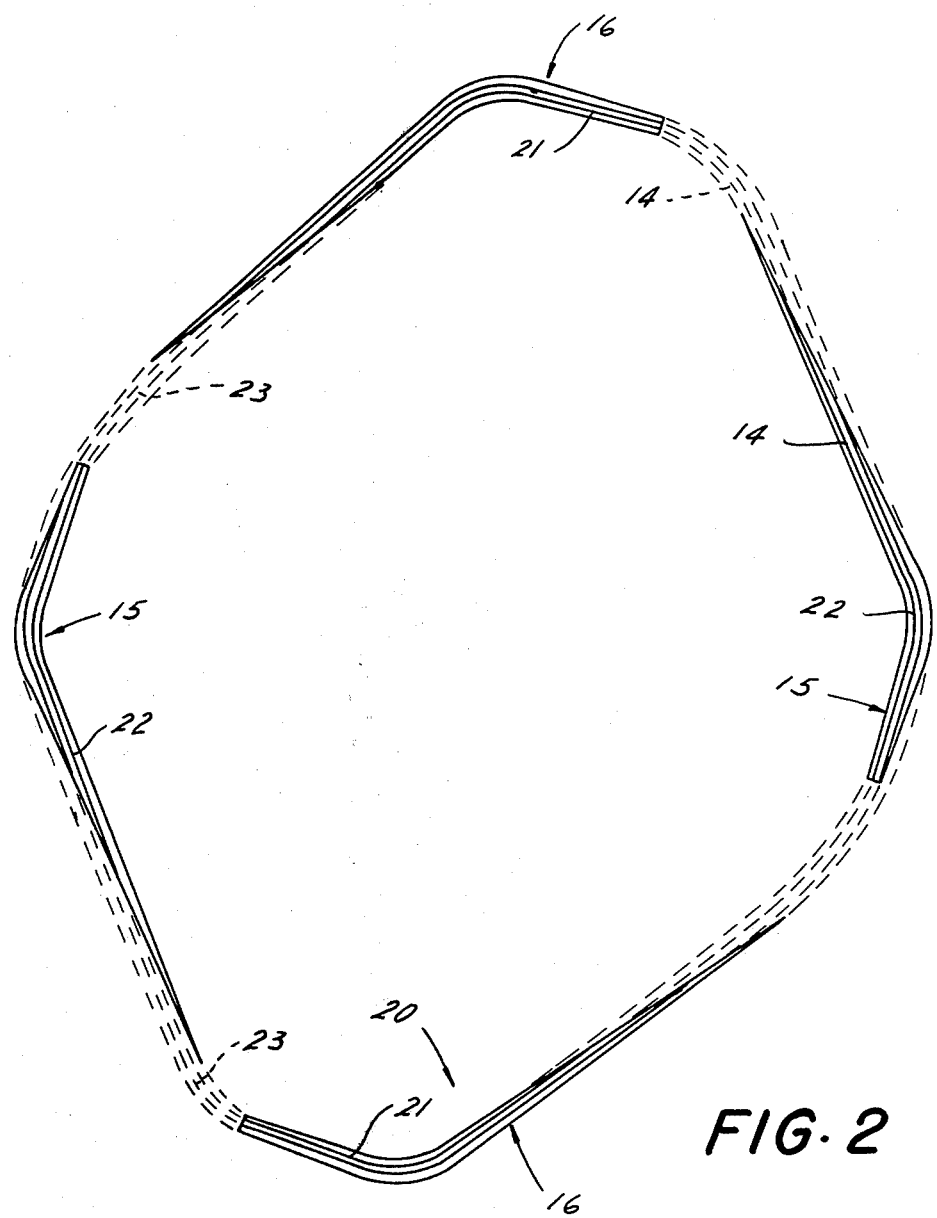

METHOD OF MANUFACTURING FIBER-REINFORCED PLASTIC BODIES

This invention relates to a method of manufacturing fiber-reinforced plastic bodies of irregular geometry with fibers extending approximately parallel to the outer contour of the body.

In fiber-reinforced plastic construction the fibers are incorporated in previously selected orientations to give specific stiffness or strength. A further aspect of fiber-reinforced plastic construction to be considered arises with bodies of bonded components of dissimilar mechanical properties. In the transmission of normal forces and bending moments between the bonded components, high peaking stresses (surface pressure, shear) arise in transitional areas where unduly abrupt changes in stiffness exist. These peaking stresses can be relieved by tapering the cross sections of the respective ends of the component (tapered overlap).

Problems of this nature occur, for example, with endoprostheses for hip joints of fiber-reinforced plastic construction, where such transitional areas are present between the bone and the shank of the prosthesis as well as between the shank and a metal head joined to it. In this instance, however, the cross-section can be tapered only at the metal head-to-shank and at the shank-to-bone transitions, but not at the cutaway point of the bone. If the sudden change in stiffness is reduced here as well, the shank must be made relatively stiff at this point. This can be achieved, for example, by means of an inner, unidirectional buildup of the composite structure to absorb the normal stresses, and enclosing it with a shell having inclined fibers to absorb shear and torsion.

The manufacture of such bodies, however, still involves considerable difficulties. Components such as the inner composite structure of the shank, where the fibers should run parallel to the respective outer contour of the shank, are rather difficult to make with optimally directed fibers, especially since the varying height of the shank will necessarily be the cause of steps in the layers of fiber along the centerline of the shank. In cases such as these, compression moulding is generally resorted to, the fibers being inserted in a mould. Inserting the fibers, however, involves a great deal of work and cost and, additionally, the fibers tend to shift positions when they are subsequently compressed, preventing a safely reproducible buildup of layers.

A broad object of the present invention is to provide a method of manufacturing fiber-reinforced plastic composite bodies of irregular geometry with a maximum of accuracy in the orientation of the fibers.

It is a particular object of the present invention to provide a method wherein fibers are used to wind a ring the contour of which conforms in sections to the contour of sections of the body to be manufactured, and wherein these ring sections are subsequently cut from the ring and then joined together to form the body. This method permits shapes of any intended geometry to be manufactured using proven winding practice.

The outer contrours of the sections of the body to be wound are projected one after the other on to a suitable ring to be formed by the layers of fiber to be wound using conventional winding methods. The constituents of the body so produced in the ring are then cut from the ring and, if necessary, are partially reformed and bonded together such that the original outer contours of the ring constituents form the outer contour of the finished shape. In this manner, a parallel relationship between the fibers and the surface of the body results automatically and very accurately from the wound product.

Further objects and advantages of the present invention are described with reference to the accompanying drawings. In the drawings:

FIG. 1 is a longitudinal cross-sectional view of an endoprosthesis for a hip joint manufactured in accordance with the method of the present invention; and FIG. 2 is a transverse cross-sectional view through a wound fiber-reinforced plastic ring according to this invention.

The endoprosthesis consists of a socket 10 and a ball 11 cooperating with it. The ball 11, which is normally made of metal, is joined to a shank 13 by a metal head 12. The shank 13, which is inserted into the hollow interior of a limb bone, is in the nature of a beam subjected to endwise pressure, flexure, shear, and torsion. To anticipate these loads and maximally adapt the stiffness of the shank to the bone, the shank is preferably a fiber-reinforced plastic construction with layers of fibers running in the longitudinal direction as well as at an angle of, e.g., ±45° with the centerline of the shank.

The longitudinally directed fibers 14 shown in the drawing should extend for the most part parallel to the outer contour 15, 16 of the shank 13. This makes for a stepwise arrangement of the layers along the centerline 17 of the shank, as will be clearly apparent from the drawing. This longitudinal composite structure is then wrapped in a layer of angularly extending fibers. The outer layer of the composite structure, not being part of the present invention, has been omitted in the drawing for clarity of presentation.

In order to manufacture a longitudinal composite structure such as the shank 13 of a prosthesis, the geometry of the two shank halves 21 and 22 resulting from a longitudinal section through the centerline 17 are projected on to a ring.

FIG. 2 illustrates such a ring 20 containing two each of the shank halves 21 and 22, respectively. The ring 20 is wound by normal winding practice. After setting, the body constituents 21 and 22 are cut away and processed mechanically at their ends for final forming.

The intermediate sections 23 of the ring, here indicated in broken lines to accentuate the body constituents, are scrapped. The inner surface of a half 21 is then bonded to the outer surface of the half 22 such that the contours 16 and 15 form the outer surface of the finished shank, giving the fibers 14 the intended direction parallel to the surface of the shank.

The method of the present invention is suitable for manufacturing composite structures for all technical applications, wherein depending on the geometry of the intended body the latter is composed of two or more suitably shaped constituents. If necessary the ring 20 can be built up using one or several pairs of constituents.

The invention has been shown and described in preferred form only, and by way of example, and many variations may be made in the invention which will still be comprised within its spirit. It is understood, therefore, that the invention is not limited to any specific form or embodiment except insofar as such limitations are included in the appended claims.

What is claimed is:

1. A method of manufacturing a fiber-reinforced plastic body having a tapering shape, comprising the steps of:
   (a) winding a ring of fibers such that different sections of the ring around its periphery correspond in contour to different longitudinal sections of the body,
   (b) cutting said sections of the ring from the remainder of the ring to form a first section having an uncut side corresponding to one side of said body and a cut side tapering with respect to said uncut side of said first section, and a second section having an uncut side corresponding to the opposite side of said body and a cut side tapering with respect to said uncut side of said second section, and
   (c) joining said first and second cut sections together along said cut sides to form the body of tapering shape having opposite sides formed from said uncut sides, whereby the fibers run approximately parallel to the outer contour of the finished body.

2. A method as defined in claim 1 wherein the cut ring sections are bonded to each other to form the body.

3. A method of forming an endoprosthesis comprising a longitudinally-extending stem portion tapering to an end for insertion into a bone, and a head portion for carrying a ball of a ball-and-socket joint, said head portion being inclined to said stem portion, said method comprising the steps of:
   (a) winding a ring of fibers such that different sections of the ring around its periphery correspond in contour to different longitudinal sections of the endoprosthesis,
   (b) cutting said sections of the ring to form a first section having an uncut side corresponding to one side of said endoprosthesis and a cut side tapering away from the uncut side along the stem portion towards the head portion, and a second section having an uncut side corresponding to the opposite side of said endoprosthesis and a cut side tapering away from the uncut side along the stem portion towards the head portion, and
   (c) joining said first and second cut sections together along said cut sides to form the endoprosthesis of tapering cross-section having opposite sides formed from said uncut sides, whereby the fibers run approximately parallel to the outer contour of the finished endoprosthesis.

4. A method of manufacturing an endoprosthesis as defined in claim 3, wherein said sections are cut so that each cut side also tapers towards said uncut side along the head portion away from said stem portion, whereby on joining of said first and second cut sections along said cut sides the head portion of the finished endoprosthesis tapers to an end remote from the stem portion.

5. A method of manufacturing an endoprosthesis as defined in claim 3 wherein the cut ring sections are bonded to each other to form the endoprosthesis.

* * * * *